United States Patent
Lee et al.

(10) Patent No.: US 11,771,914 B2
(45) Date of Patent: Oct. 3, 2023

(54) LASER THERAPY DEVICE AND LIGHT TRANSMITTING MEMBER

(71) Applicant: LUTRONIC CORPORATION, Goyang (KR)

(72) Inventors: Hee Chul Lee, Goyang (KR); Sung Jin Lim, Goyang (KR)

(73) Assignee: LUTRONIC CORPORATION, Goyang (KR)

( * ) Notice: Subject to any disclaimer, the term of this patent is extended or adjusted under 35 U.S.C. 154(b) by 0 days.

(21) Appl. No.: 17/265,458

(22) PCT Filed: Jul. 29, 2019

(86) PCT No.: PCT/KR2019/009381
§ 371 (c)(1),
(2) Date: Feb. 2, 2021

(87) PCT Pub. No.: WO2020/027514
PCT Pub. Date: Feb. 6, 2020

(65) Prior Publication Data
US 2021/0228902 A1 Jul. 29, 2021

(30) Foreign Application Priority Data
Aug. 3, 2018 (KR) .................. 10-2018-0090896

(51) Int. Cl.
*A61N 5/06* (2006.01)
*A61N 5/067* (2006.01)

(52) U.S. Cl.
CPC ............ *A61N 5/0616* (2013.01); *A61N 5/067* (2021.08); *A61N 2005/0633* (2013.01); *A61N 2005/0665* (2013.01)

(58) Field of Classification Search
CPC ..... A61N 5/067; A61N 5/0616; A61N 5/0633
See application file for complete search history.

(56) References Cited

U.S. PATENT DOCUMENTS 4,697,590 A * 10/1987 Nakai .................. A61B 18/203
362/401
5,554,156 A * 9/1996 Shimizu ............... A61B 18/203
606/17

(Continued)

FOREIGN PATENT DOCUMENTS

JP 06-277227 A 10/1994
JP 2014-164818 A 9/2014

(Continued)

OTHER PUBLICATIONS

International Search Report dated Oct. 23, 2019 for International Patent Application No. PCT/KR2019/009381.

*Primary Examiner* — James M Kish
*Assistant Examiner* — Jessica L Mullins (57) ABSTRACT

The present invention relates to a laser therapy device and a light transmitting member comprising: a main body provided with a laser light source; a light irradiation unit for irradiating a laser generated in the laser light source to a treatment site; and a light transmitting unit provided between the main body and the light irradiation unit so as to form a path through which the laser is transmitted, wherein the light transmitting unit comprises a plurality of arm members connected by joint parts, and at least one of the plurality of arm members has therein a vacuum forming unit at a position where the laser is focused. According to the present invention, by configuring a compact structure, it is possible to improve the quality of a laser outputted to a treatment site.

15 Claims, 6 Drawing Sheets

(56) References Cited

U.S. PATENT DOCUMENTS

2013/0268031 A1    10/2013  Ko
2014/0235918 A1     8/2014  Kakutani et al.

FOREIGN PATENT DOCUMENTS

| KR | 10-1269970 B1 | | 5/2013 |
|----|---------------|---|--------|
| KR | 20130099330   | * | 9/2013 |
| KR | 20130099330 A |   | 9/2013 |
| KR | 20180052867   | * | 5/2018 |
| KR | 20180052867 A |   | 5/2018 |
| KR | 101855214 B1  |   | 6/2018 |

* cited by examiner

LASER THERAPY DEVICE AND LIGHT TRANSMITTING MEMBER

TECHNICAL FIELD

The present disclosure relates to a laser therapy device and a light-transmitting member and, more particularly, to a laser therapy device and a light-transmitting member for improving the quality of a laser used for treatment.

BACKGROUND ART

Recently, technology for treating tissue by transmitting therapeutic energy to human tissue to change the condition of the tissue or remove the tissue has been widely applied. Specifically, therapy devices using various types of electromagnetic energy sources, such as laser beams, flash lamps, radio frequency waves, microwaves, or ultrasound are commercially available.

Particularly, a therapy device using a laser is widely used as a device for treating skin lesions. Such a device is disclosed in Korean Patent Publication No. 10-1269970. When tissue is irradiated with the laser using the therapy device, the laser is absorbed by specific tissue such as collagen, a hair follicle, or hemoglobin according to the wavelength characteristics of the laser to transmit energy thereto. As the tissue absorbs the energy, the condition of the tissue is changed, and thus, the tissue is treated.

Generally, the laser therapy device is configured such that a laser is generated from a laser light source, moves to a handpiece along a set light path, and is radiated through the handpiece to a treatment site. Here, some of a laser light path includes a section in which the laser is concentrated, focused, and then diffused again. While the laser passes through this section, the cross-sectional characteristics of the laser may be uniformly adjusted. However, in the section where the laser is focused, the energy of the laser is concentrated. Due to the high energy, adjacent air, gas, or suspended substances are ionized, and the generated ions lead to deterioration in quality of the passing laser.

DISCLOSURE

Technical Problem

The present disclosure is to provide a laser therapy device and a light-transmitting member, capable of preventing the quality of a laser from being deteriorated even in the case of using a high power laser, when a light path having a laser focusing area is formed.

Technical Solution

In order to solve the aforementioned problem, the present disclosure proposes a laser therapy device, including a main body provided with a laser light source; a light irradiation unit for irradiating a treatment site with a laser generated in the laser light source; and a light-transmitting unit provided between the main body and the light irradiation unit so as to form a path through which the laser is transmitted, wherein the light-transmitting unit may include a plurality of arm members connected by joint parts, and at least one of the plurality of arm members may have therein a vacuum forming unit at a position where the laser is focused.

Specifically, the at least one arm member may include a pair of focusing elements for focusing the laser at a position where the vacuum forming unit is provided, and the pair of focusing elements may be installed at both ends of the arm member adjacent to the joint part, respectively.

The laser therapy device may further include an alignment unit installed on each of both ends of the at least one arm member or the joint part, and adjusting an alignment state of the focusing element to adjust a position on which the laser is focused.

The focusing element may comprise a concave mirror for focusing the laser while reflecting the laser transmitted through the joint part. A focal distance of the concave mirror may range from 5 mm to 10000 mm.

A vacuum module may be installed in the at least one arm member, and the vacuum module may form a vacuum forming unit in the arm member.

The vacuum module may include a body defining therein a vacuum area on which the laser is focused, windows provided on both ends of the body to allow the laser to pass therethrough, and a sealing member provided along an edge of each of the windows to maintain a vacuum state of the vacuum area.

The vacuum module may further include fastening units provided on both sides of the body to fix the windows, and a spacer disposed between each of the fastening units and each of the windows to distribute stress transmitted to the window.

Furthermore, in order to solve the aforementioned problem, the present disclosure proposes a light-transmitting member provided between a main body and a handpiece of a laser therapy device and having therein a path in which a laser is transmitted, the light-transmitting member including a plurality of arm members rotatably connected at both ends thereof between the main body and the handpiece via a plurality of joint parts, and a vacuum forming unit provided in at least one of the plurality of arm members at a position where the laser is focused, thus defining a vacuum area.

Advantageous Effects

In accordance with the present disclosure, it is advantageous in that a vacuum forming unit is formed in a laser focusing area on a light path, thus preventing the quality of a laser from being deteriorated.

Further, such a vacuum forming unit is provided not on a laser main body but on an arm member, so that it is possible to more compactly make the laser main body, and to improve the quality of a laser outputted to a handpiece.

Furthermore, the vacuum forming unit is formed as a separate module and then is installed in the arm member, thus improving the convenience of manufacture and maintenance.

Moreover, it is possible to improve response to various wavelengths of the laser by using a concave mirror which has focusing elements for focusing a laser on both ends of the arm member, and it is possible to improve response to machining errors by adjusting the alignment of the focusing element in a state in which machining is completed.

MODE FOR DISCLOSURE

Hereinafter, a laser therapy device in accordance with an embodiment of the present disclosure will be described in detail with reference to the accompanying drawings. In the following description, the positional relationship between respective components will be described in principle on the basis of drawings. Furthermore, the drawings may simplify or exaggerate the structure of the present disclosure for the convenience of description. Thus, the present disclosure may add, change, or omit various devices without being limited thereto.

Hereinafter, a "laser therapy device" includes all types of laser therapy devices for treating mammals as well as humans. In other words, the laser therapy device includes various types of therapy devices which are used for treating various lesions or improving tissue conditions using a laser as an energy source.

Hereinafter, the term "treatment site" refers to a tissue requiring treatment among various bodily organs of the mammal as well as the human. Although skin tissue will be mainly described below as the treatment site, the present disclosure is not limited thereto.

Hereinafter, a laser therapy device in accordance with an embodiment of the present disclosure will be described with reference to FIGS. 1 and 2.

Figure 1:
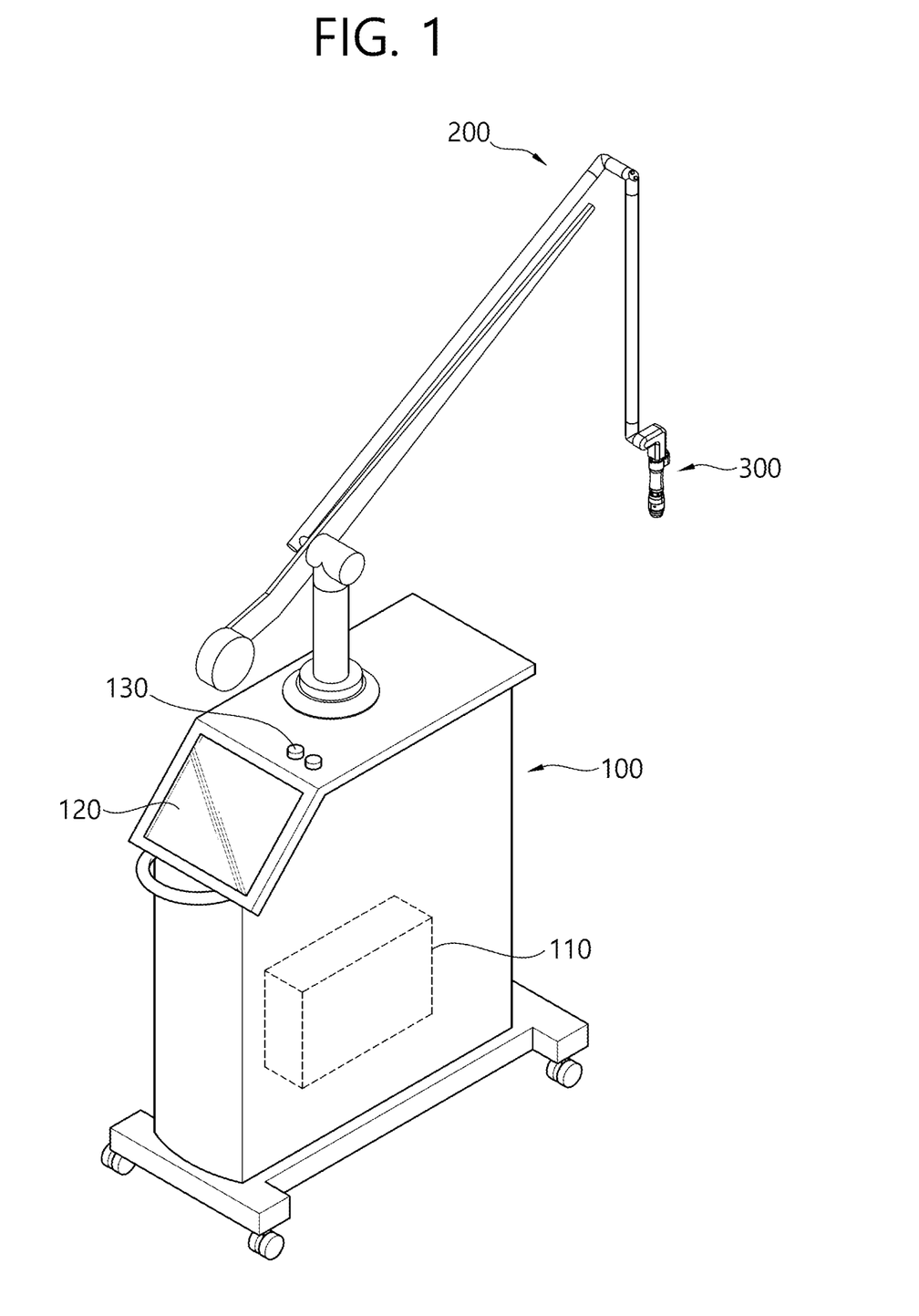
FIG. 1 is a perspective view illustrating a laser therapy device in accordance with an embodiment of the present disclosure.

FIG. 1 is a perspective view illustrating a laser therapy device in accordance with an embodiment of the present disclosure. As shown in FIG. 1, the laser therapy device in accordance with this embodiment includes a therapy-device main body 100, a handpiece 300, and a light-transmitting unit 200 connecting the main body and the handpiece.

The main body 100 defines the main skeleton of the laser therapy device, so that various components are installed therein. A laser light source 110 for generating a laser and various optical elements for transmitting the laser are provided in the main body. A control panel 120 for operating the therapy device or setting operational content and a display 130 for displaying various pieces of information may be mounted on an outer surface of the main body.

Here, the laser light source 110 may be configured in a structure which oscillates a laser using a laser medium and a resonator. The laser medium may be determined based on a wavelength selected in consideration of the treatment purpose, and may use Nd;YAG, Alexandrite, etc. However, it is possible to use laser light sources other than the laser resonator structure, for example, a laser diode. The laser generated from the laser light source is transmitted through various optical elements (not shown) to the light-transmitting unit 200 and the handpiece 300.

The handpiece 300 forms the end structure of the laser therapy device, and serves as a light irradiation unit which irradiates the treatment site with the laser generated from the laser light source of the main body 100. The handpiece 300 is configured in a shape which may be held by a user's hand, and the user performs the treatment while changing the treatment site with the handpiece held by his or her hand. An operation unit is provided on the outer surface of the handpiece 300 to control the operation of the handpiece, and in addition, sensors for detecting various pieces of information during treatment may be installed.

The light-transmitting unit 200 is provided between the above-described main body 100 and handpiece 300 to form a light path along which the laser is transmitted. In other words, the laser generated from the laser light source of the main body 100 is transmitted through the light-transmitting unit 200 to the handpiece 300, and then is radiated to the treatment site. Such a light-transmitting unit 200 may be formed in the shape of a cable using the optical element such as optical fiber. In this embodiment, the light-transmitting unit may be composed of a plurality of arm members 210 which are bendably connected to each other. A reflective member 240 is provided in each arm member 210, and the laser is reflected by the reflective member 240 of each arm member 210 to be transmitted along the internal light path to the handpiece 300.

Specifically, as shown in FIG. 1, the light-transmitting unit 200 of this embodiment may include two arm members 210a and 210b. Each arm member 210a or 210b is connected at both ends thereof to a joint part 220, and is rotatably connected via the joint part 220 to the main body 100, the handpiece 300, or another arm member. Thus, if a user moves the handpiece 300 during treatment, each arm member 210a or 210b pivots about each joint part 220 to correspond to the movement of the handpiece.

Figure 2:
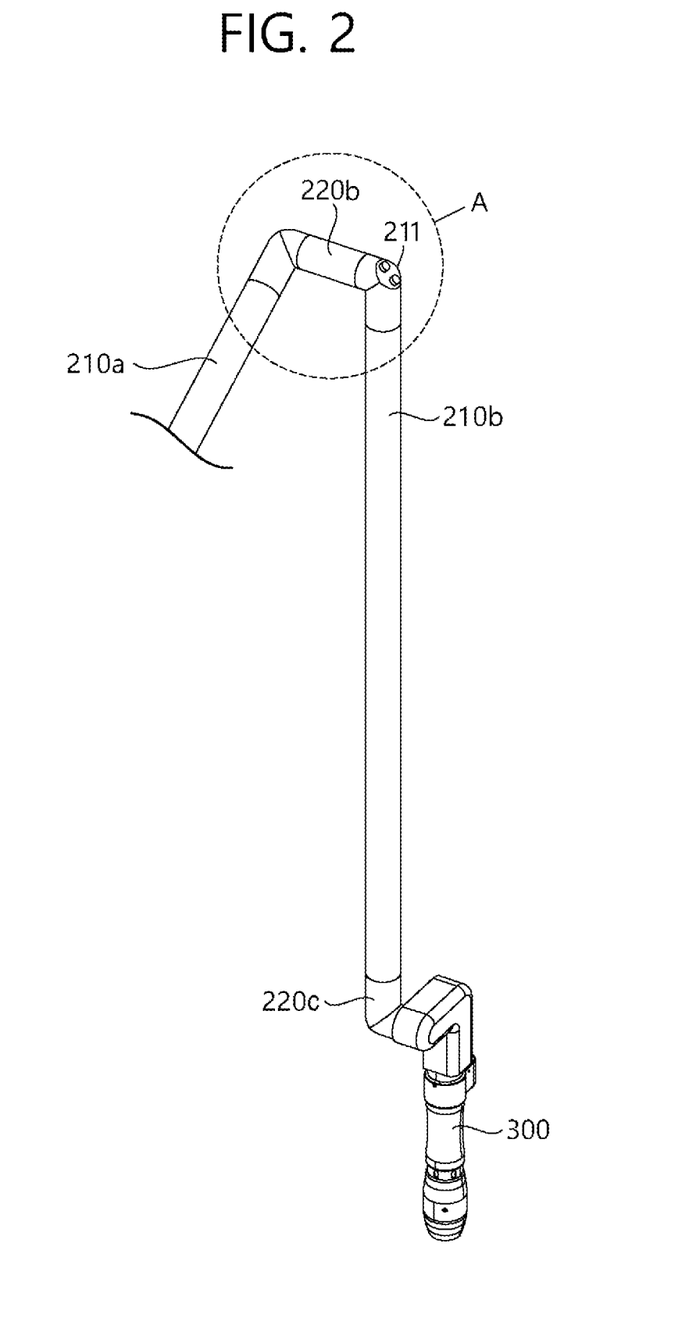
FIG. 2 is a perspective view illustrating a connecting structure of a first arm member and a second arm member shown in FIG. 1.

FIG. 2 is a perspective view illustrating a connecting structure of the first arm member 210a and the second arm member 210b shown in FIG. 1. As shown in FIG. 2, a first end of the first arm member 210a and a first end of the second arm member 210b are connected via a joint part 220b. Each of the first arm member 210a and the second arm member 210b is rotatably connected to the joint part 220b, so that each of the first arm member 210a and the second arm member 210b is relatively rotated. Furthermore, a second end of the first arm member 210a is rotatably connected to the main body 100 via the joint part 220a, and a second end of the second arm member 210b is rotatably connected to the handpiece 300 via the joint part 220c.

Meanwhile, a hollow part corresponding to a laser travel path is formed in each arm member 210 in a longitudinal direction of the arm member. Moreover, bent parts 211 are formed on both ends of each arm member 210 to change the laser travel direction, and the reflective member 240 is provided in each bent part to reflect the laser. Thus, while the direction of the laser transmitted from the laser light source of the main body 100 is sequentially changed by the reflective members 240 provided on both ends of each arm member, the laser may be transmitted through the first arm member 210a and the second arm member 210b to the handpiece 300.

Figure 3:
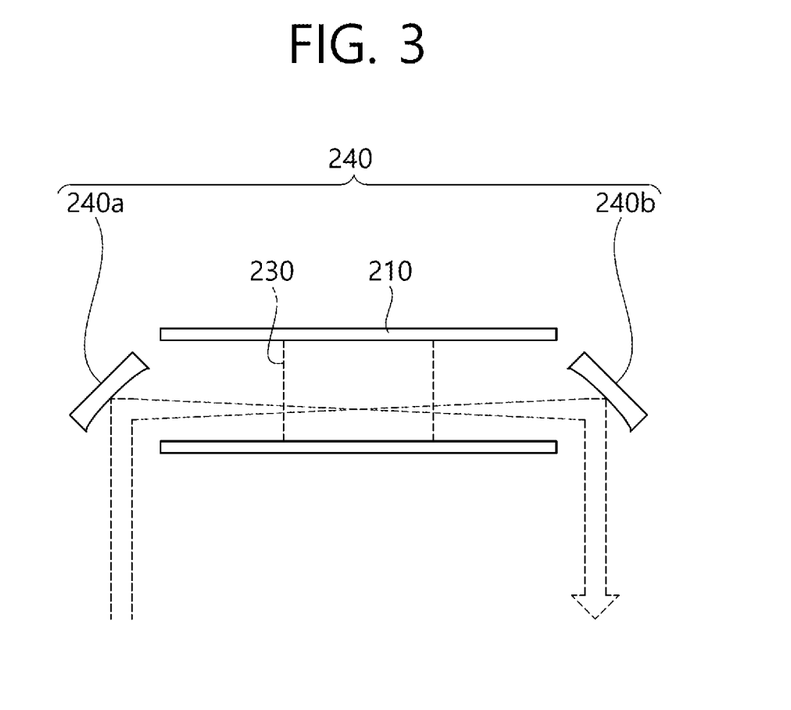
FIG. 3 is a diagram schematically illustrating an internal structure of any one of the arm members shown in FIG. 1.

Specifically, as shown in FIGS. 2 and 3, the reflective members 240a and 240b are installed, respectively, in the bent parts 211 provided on both ends of the arm member 210. The reflective member 240 is inclined at an angle of 45 degrees with respect to the laser travel direction. Thus, the reflective member may reflect the laser to change the laser travel direction by 90 degrees. Therefore, the laser whose travel direction is changed by 90 degrees by the reflective member 240a provided on the first end of the first arm member 210a passes through the joint part 220b having the hollow part therein, and then the laser travel direction is changed again by 90 degrees by the reflective member 240b provided on the first end of the second arm member 210b, so that the laser may travel in the longitudinal direction of the second arm member 210b. In this case, if the first arm member 210a and the second arm member 210b pivot about the joint part 220b, the reflective members 240a and 240b adjacent to the joint part may also be relatively rotated to maintain the light path.

Although FIG. 2 illustrates the rotating method via the joint part and the laser travel path, focused on the connecting part between the first arm member and the second arm member, a part where the main body 100 and the first arm member 210a are connected and a part where the second arm member 210b and the handpiece 300 are connected are also configured in a manner similar to that of FIG. 2, but a detailed description thereof is omitted to avoid duplication. Meanwhile, in this embodiment, a structure in which the light-transmitting unit is composed of two arm members is mainly described. However, the present disclosure is not limited thereto, but the light-transmitting unit may be composed of three or more arm members.

Furthermore, although not shown in the drawings in detail, signal lines may be included to transmit various control signals generated from a control unit of the main body or the operation unit of the handpiece, between the main body and the handpiece, along the light-transmitting unit.

FIG. 3 is a diagram schematically illustrating an internal structure of any one of the arm members shown in FIG. 1. As shown in FIG. 3, the laser therapy device in accordance with this embodiment may be configured to have a laser focus position F in at least one arm member 210. Here, the focus position F refers to a position on which the laser is focused. As shown in FIG. 3, by passing through a path where the laser is focused on the light path and then is diffused again, the sectional characteristics of the laser may be uniformly adjusted, and the quality of the laser generated from the laser light source may be improved as much as possible, even when the quality is not good.

Such a focus position F may be provided on the light path provided in the main body, but there is a high possibility that the sectional characteristics of the laser are also changed as the laser travels along the light path later. On the other hand, if the focus position is formed on the arm member as in this embodiment, the arm member is relatively adjacent to a position where the laser is radiated to the outside, so that it is possible to output while maintaining the uniform laser sectional characteristics. Furthermore, it is advantageous in that the main body can be compactly made.

Meanwhile, in order to form the focus position F in the arm member 210, a focusing element is required to focus the laser. For instance, in this embodiment, the above-described reflective members 240 provided on both ends of the arm member 210 may be configured to serve as a focusing element. Specifically, the reflective members 240a and 240b provided on both bent parts of the arm member are formed of the reflective members each having a concave reflective surface, so that the laser is reflected through the reflective surface and simultaneously the reflected laser is focused.

Thus, in the case of using the reflective members 240a and 240b of the arm member 210 as the focusing element, it is advantageous in that the number of optical elements required for the light path is minimized as compared with a configuration having a separate condensing lens, thus realizing a compact structure. Furthermore, if the condensing lens is used as the focusing element, a difference in focal distance and chromatic aberration occur according to the wavelength of the laser due to a difference in refractive index depending on the wavelength of light, so that the quality of the output laser may deteriorate. In contrast, this embodiment using the reflective member as the focusing element is advantageous in that it is not configured to transmit a corresponding element and focus light, so that it is possible to minimize deterioration in quality of the output laser according to the wavelength, even if the laser light source of various wavelengths is used.

Therefore, in this embodiment, the concave mirror 240 may be used as the reflective member as well as the focusing element. Specifically, in this embodiment, a parabolic optical material may be used as the reflective member as well as the focusing element.

Here, the focal distance of the reflective member may range from 5 mm to 10000 mm, and more preferably, the concave mirror having the focal distance of 100 mm to 1000 mm may be used. Furthermore, the reflective member may be subjected to surface treatment such as coating to have high reflectivity for the wavelength of the laser which is used. However, the present disclosure may use various structures without being limited thereto.

Meanwhile, as shown in FIG. 3, at least one arm member 210 has therein a focus position F on which the laser is focused, and a vacuum forming unit V is provided in the corresponding focus position. As described above, if the laser is focused and diffused by the focusing element 240, the energy of the laser concentrates on the focus position. Therefore, if general air is located at such a focus position, gas or suspended substances contained in the air are ionized. If such substances are present in the light path, there is a problem where the quality of the transmitted laser rapidly deteriorates. Therefore, in this embodiment, the vacuum forming unit V is formed at the focus position F on which energy concentrates, thus preventing gas or suspended substances from being ionized.

Here, the term "vacuum" is not limited to an absolute vacuum state, and may include a state in which pressure is lowered to the extent that there is a difference from the atmospheric pressure, or a state in which the distribution density of the gas is lowered compared to the atmospheric pressure.

Figure 4:
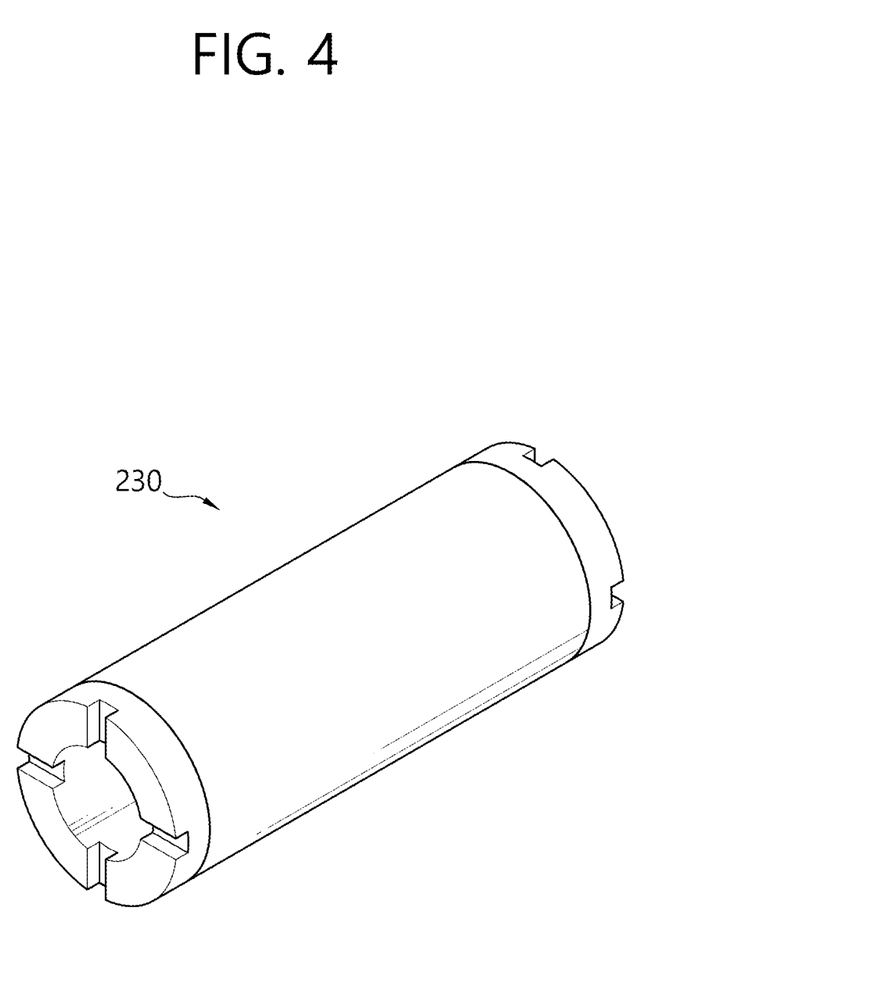
FIG. 4 is a perspective view illustrating a vacuum module constituting a vacuum forming unit.

Hereinafter, the structure of the vacuum forming unit V in accordance with this embodiment will be described in detail with reference to FIGS. 4 and 5. FIG. 4 is a perspective view illustrating a vacuum module 230 constituting a vacuum forming unit, and FIG. 5 is a sectional view illustrating a section of the vacuum module of FIG. 4 installed in the arm member.

The above-described vacuum forming unit V may be configured in various structures at a focus position inside the arm member. For instance, the vacuum forming unit V may be formed as a structure integral with the arm member inside the arm member. However, in this embodiment, the separate vacuum module is manufactured as shown in FIG. 4, and then is installed in the arm member as shown in FIG. 5. In the case of using the separate vacuum module 230 as in this embodiment, manufacture as well as separation for the purpose of repair or replacement is easy, so that it is advantageous in terms of maintenance and repair.

Figure 5:
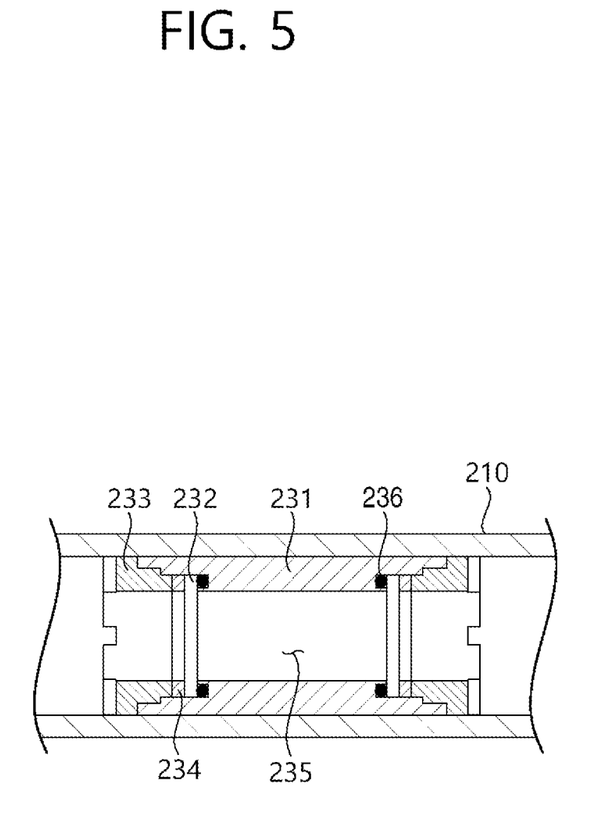
FIG. 5 is a sectional view illustrating a section of the vacuum module of FIG. 4 installed in the arm member.

As shown in FIG. 5, the vacuum module 230 includes a body 231 in which a vacuum area is formed, windows 232 which are provided on both ends of the body to allow laser to pass therethrough, and fastening units 233 which are provided on both sides of the body to fix the windows.

The body 231 is configured to have an appearance similar to the internal structure of the arm member 210 to be installed in the arm member, and in this embodiment, is configured to have a cylindrical structure as an example. The body has a hollow part therein to define the vacuum area 235. The body 231 may be installed in the arm member 210 so that the focus position F is located in the vacuum area 235.

Moreover, the windows 232 are installed on both sides of the body to form a path through which the laser passes. The window 232 may be made of a transparent material to allow the laser to be transmitted, and specifically, may be made of transparent glass with special coating.

Therefore, the laser incident on the vacuum module 230 passes through one window in a focusing form, is focused on the vacuum area inside the body, and subsequently is diffused and passes through one window.

Meanwhile, the fastening units 233 are configured to fix the windows 232 to both sides of the body 231, and may be configured using various structures such as bonding, press-fitting, or bolting. However, the fastening unit 233 of this embodiment may be configured in a ring-nut structure which is screwed to the cylindrical body 231. The pair of windows 232 is coupled to both sides of the body 231 by the fastening units 233 to serve as a cover for maintaining vacuum in the body.

Moreover, the vacuum module 230 may further include an O-ring 236 provided between the body 231 and the window 232 so as to maintain a vacuum state in the vacuum area 235. A recess is provided in a side of the body in which the window is seated to dispose the O-ring 236 along the edge of the window. If the window is installed with the O-ring 236 being disposed in the recess, a gap between the window 232 and the body 231 is sealed by the O-ring 236, thus maintaining a vacuum state therein.

Furthermore, a separate spacer 234 may be further provided between the window 232 and the fastening unit 233. Such a spacer 234 serves as a buffer in the process of fastening the fastening unit, thus preventing torsion stress from being transmitted to the window and preventing the O-ring from being twisted.

However, although this embodiment shows a sealing structure using the O-ring, an interior may be sealed to maintain vacuum using sealing members other than the O-ring or using a method such as bonding or bolting.

As described above, in this embodiment, the vacuum forming unit is provided on the focus position of the arm member using the above-described vacuum module, thus preventing gas or suspended substances from being ionized.

In this embodiment, the vacuum forming unit is installed in the form of a separate module in the arm member. However, such a vacuum forming unit may be provided on the arm member itself when the arm member is manufactured.

Such a vacuum forming unit may be provided on one arm member (e.g. the second arm member) among the plurality of arm members, and a separate vacuum forming unit may be provided on each of all arm members.

Figure 6:
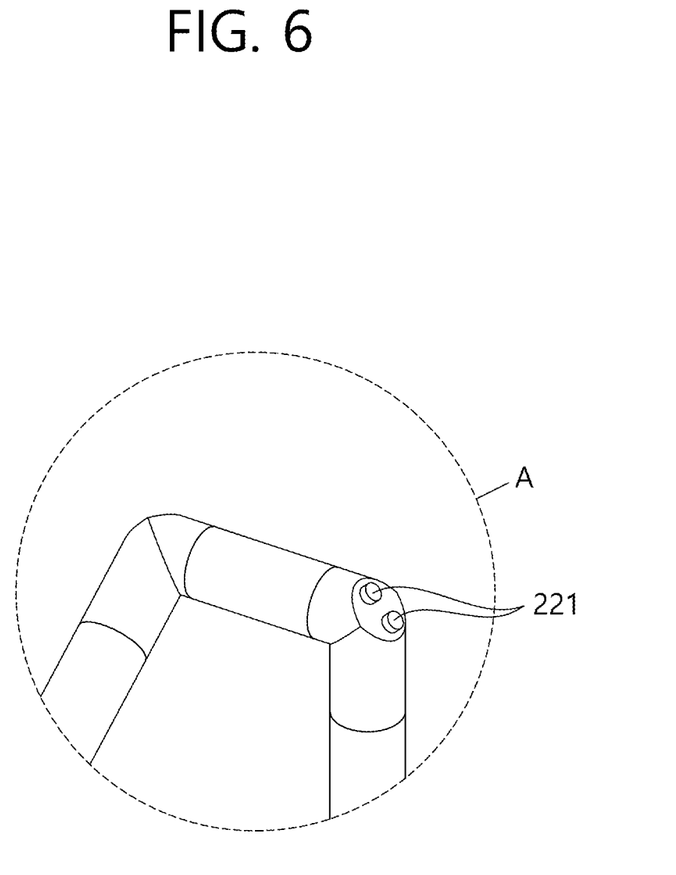
FIG. 6 is an enlarged view illustrating part A in FIG. 2.

FIG. 6 is an enlarged view illustrating part A in FIG. 2. As shown in FIG. 6, an alignment unit 221 may be further provided on the outside of the bent part 211 of the arm member 210. The alignment unit 221 may be installed to be directly/indirectly operated in conjunction with the reflective member located inside the bent part to adjust the position and direction in which the concave mirror is disposed. For example, if any one element of the alignment unit is rotated, the position of a support unit which supports the concave mirror is changed, so that the direction of the concave mirror may be changed. As such, various alignment adjusting methods may be used.

If the condensing lens installed in the arm member is used as the focusing element, it is impossible to align the focus position with the position of the vacuum forming unit after the therapy device is manufactured. In contrast, in this embodiment, since the focusing elements 240a and 240b are disposed on the bent parts 211 provided on both ends of the arm member, it is possible to finely adjust the position and direction of the focusing element using the alignment unit which is exposed to the outside of each bent part. Therefore, it is advantageous in that it is possible to perform alignment related to the focus position due to manufacturing tolerances or impact during use without the necessity of disassembling the therapy device.

Although preferred embodiments of the present disclosure have been described in detail, the present disclosure is not limited to the above embodiments. It is apparent to those skilled in the art that many modifications or changes may be made without departing from the scope of the present disclosure defined in the accompanying claims.

The invention claimed is:

1. A laser therapy device comprising:
a main body provided with a laser light source;
a light irradiation unit for irradiating a treatment site with a laser generated in the laser light source; and
a light-transmitting unit provided between the main body and the light irradiation unit so as to form a path through which the laser is transmitted,
wherein the light-transmitting unit comprises a plurality of arm members connected by joint parts,
wherein at least a first arm member of the plurality of arm members comprises a pair of focusing elements installed at both ends of the arm member, respectively, for focusing the laser, and a vacuum module located between the pair of focusing elements and having a vacuum area therein, the laser is focused at a position where the vacuum module is provided, the position at which the laser is focused lies entirely inside the vacuum module, and the pair of focusing elements are disposed outside and independent from the vacuum area,
wherein a portion of the path between the pair of focusing elements where the vacuum module is located is in a vacuum state by the vacuum module.

2. The laser therapy device of claim 1,
wherein the pair of focusing elements are installed at both ends of the at least first arm member adjacent to the joint part, respectively.

3. The laser therapy device of claim 2, further comprising:
an alignment unit installed on each of both ends of the at least first arm member or the joint part, and adjusting an alignment state of each of the pair of focusing elements to adjust a position on which the laser is focused.

4. The laser therapy device of claim 2, wherein each of the pair of focusing elements comprises a reflective member having a concave reflective surface for focusing the laser while reflecting the laser transmitted through the joint part.

5. The laser therapy device of claim 4, wherein each of the pair of focusing elements is an optical element having a parabolic structure.

6. The laser therapy device of claim 4, wherein a focal distance of the reflective member ranges from 5 mm to 10000 mm.

7. The laser therapy device of claim 1, wherein the vacuum module is installed entirely inside the at least first arm member and separable from the at least first arm member for repair or replacement.

8. The laser therapy device of claim 7, wherein the vacuum module comprises:

a body defining therein the vacuum area on which the laser is focused;

windows provided on both ends of the body to allow the laser to pass therethrough; and a sealing member provided along an edge of each of the windows to maintain a vacuum state of the vacuum area, where in the windows are positioned between the pair of focusing elements.

9. The laser therapy device of claim 8, wherein the vacuum module further comprises:

fastening units provided on both sides of the body to fix the windows; and a spacer disposed between each of the fastening units and each of the windows to distribute stress transmitted to the window.

10. The laser therapy device of claim 1, wherein each of two adjacent arm members among the plurality of arm members has therein a vacuum module.

11. A light-transmitting member provided between a main body and a handpiece of a laser therapy device, and having therein a path in which a laser is transmitted, the light-transmitting member comprising:

a plurality of arm members rotatably connected at both ends thereof between the main body and the handpiece via a plurality of joint parts; and a vacuum module provided in at least a first arm member of the plurality of arm members at a position where the laser is focused, the position at which the laser is focused lying entirely inside the vacuum module, the vacuum module having a vacuum area therein, wherein the at least first arm member of the plurality of arm members comprises a pair of focusing elements installed at both ends of the arm member, respectively, for focusing the laser, the vacuum module is arranged to form a portion of the path between the pair of focusing elements, and the pair of focusing elements are disposed outside and independent from the vacuum area.

12. The light-transmitting member of claim 11, wherein the pair of focusing elements are installed at both ends of the at least first arm member to be adjacent to the joint part, respectively.

13. The light-transmitting member of claim 12, wherein each of the pair of focusing elements is an off-axis parabolic mirror.

14. The light-transmitting member of claim 12, wherein the vacuum module is installed entirely inside the at least one arm member, and the vacuum module comprises a body defining therein the vacuum area on which the laser is focused, windows provided on both ends of the body to allow the laser to pass therethrough, and a sealing member provided along an edge of each of the windows to maintain a vacuum state of the vacuum area.

15. A laser therapy device comprising:

a main body provided with a laser light source;

a light irradiation unit for irradiating a treatment site with a laser generated in the laser light source; and a light-transmitting unit provided between the main body and the light irradiation unit so as to form a path through which the laser is transmitted, wherein the light-transmitting unit comprises a plurality of arm members connected by joint parts, wherein the plurality of arm members comprises a first arm member, the first arm member including a pair of focusing elements installed at both ends of the first arm member, respectively, for focusing the laser, and a vacuum module located between the pair of focusing elements and having a vacuum area therein, and the laser is focused at a position where the vacuum module is provided, the position at which the laser is focused lying entirely inside the vacuum module, and wherein a portion of the path between the pair of focusing elements where the vacuum module is located is in a vacuum state by the vacuum module, and the pair of focusing elements are disposed outside and independent from the vacuum area.

\* \* \* \* \*